Aug. 1, 1972 W. H. JESSEL, JR., ET AL Plant Pat. 3,248
CHRYSANTHEMUM PLANT
Filed Dec. 3, 1970
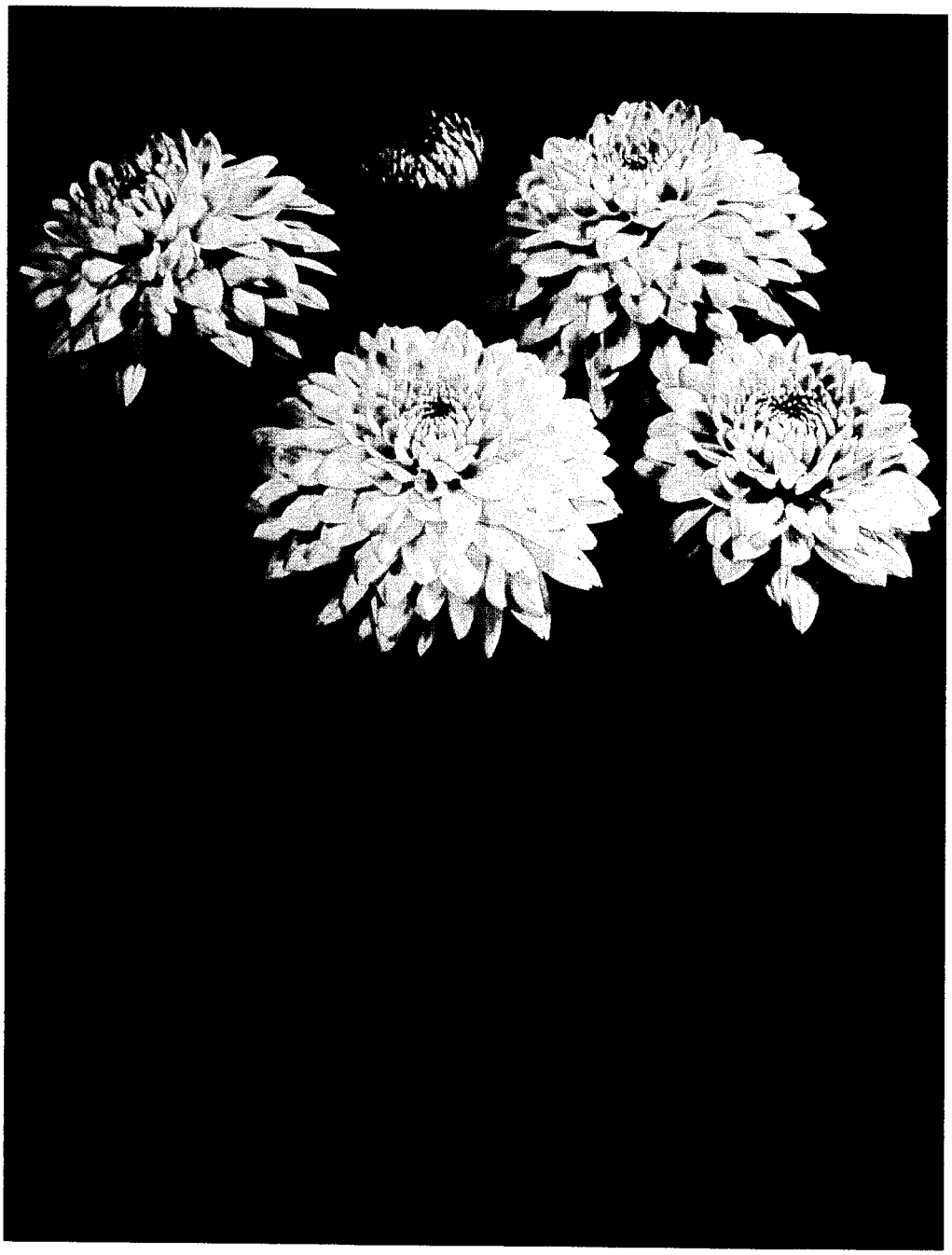

United States Patent Office

Plant Pat. 3,248

Patented Aug. 1, 1972

3,248

CHRYSANTHEMUM PLANT

Walter H. Jessel, Jr., Doylestown, and William E. Duffett, Akron, Ohio, assignors to Yoder Brothers, Inc., Barberton, Ohio

Filed Dec. 3, 1970, Ser. No. 95,000

Int. Cl. A01h *5/00*

U.S. Cl. Plt.—80 1 Claim

The present invention comprises a new and distinct cultivar of chrysanthemum plant which is a seedling of #61186–5 x #621100–7. Both parents are unpatented and identified for breeding purposes by these numbers.

The new cultivar is similar in many respects to Carillon, an unpatented but commercially well-known cultivar of Yoder Brothers, Inc., Barberton, Ohio, assignee of the present invention. The new cultivar has the same characteristics as Carillon of:

1. Rigid habit.
2. Terminal sprays.
3. Uniform response.

The new cultivar is distinguished from Carillon by the following characteristics:

1. Flowers approximately one inch larger with a higher crown.
2. More decorative flower form.
3. A lighter flower color with less lavender tones.
4. A more pointed petal tip.
5. Longer, broader more deeply indented foliage, with more prominent veins.
6. Darker foliage color.
7. More coarse serration to the leaf margin.
8. Smaller stipules.
9. One week later response.
10. A more limited flowering period primarily designed for mid-winter performance.

The new cultivar was selected from the progency of the designated cross, and when asexually reproduced by cuttings at Barberton, Ohio, has been found to retain its distinctive characteristics through successive propagations.

The new cultivar when grown in the vicinity of Barberton, Ohio, has a response period of approximately 11 weeks, although it will be understood that the response time, blooming period, color, and total vigor may vary significantly with varying environmental conditions such as temperature, day length, and light intensity.

The accompanying drawing shows the unique characteristics of the new cultivar, the color being as nearly true as possible with color illustrations of this type.

The following description is based on observations made of the new cultivar in a greenhouse in Barberton, Ohio. Color references are to the Munsell Color Book, 1963 edition, and comparisons made where differences exist with the cultivar Carillon.

| | Caravelle | Carillon |
|---|---|---|
| Bloom: | | |
| Size | 2½″ | 1⅝″. |
| Fully expanded | 3″ | 1⅞″. |
| Borne | Clusters on elongated pedicels. | Clusters on elongated pedicels. |
| Stems | Strong | Strong. |
| Form | Decorative | Formal. |
| Permanence | 10–12 days | 10–12 days. |
| Color: | | |
| Center of flower. | Light greenish yellow, 10Y9/4. | Pale lavender, 10RP9/1. |
| Base of petals | Lavender pink, 10P7/8 to lavender pink, 10P8/6. | Lavender, 10P9/6 to lavender pink, 10P7/8. |
| Inside of petals | do | Do. |
| Reverse of petals. | Lavender pink | Lavender. |
| Tonality from a distance. | do | Do. |
| Discoloration | Lavender pink, 10P8/6. | Lavender pink, 10P7/8. |
| Petals: | | |
| Texture | Smooth | Smooth. |
| Appearance and form. | Open at base, broad ridged shallow keel—tapering to a sharp point. | Open at base, broad deep keel, inward lateral roll tapering to a blunt point. |
| Arrangement | Composite, whorled on a single receptacle. | Composite, whorled on a single receptacle. |
| Persistence | Resist shatter | Resist shatter. |
| Fragrance | Typical chrysanthemum. | Typical chrysanthemum. |
| Peproductive organs: | | |
| Stamen, anthers | 0–10 | None. |
| Pollen | None to very scant | Do. |
| Arrangement | Clustered in center of flower, if present. | |
| Styles | Present both ray and disc florets. | |
| Length | Short. | |
| Ovaries | At the base of petal attached to receptacle. | |
| Rant: | | |
| Form | Herbaceous. | |
| Growth | Upright. | |
| Height | 42″, depending on culture (Carillon, by way of comparison is 46″) | |
| Spread | None when grown single stem to slight when grown pinched. | |
| Foliage: | | |
| Top side | Very dark green, 10GY2/4. | Dark green, 7.5GY3/4. |
| Size | 5½″ long, 3″ wide | 4¾″ long, 2⅛″ wide. |
| Quantity | Numerous | Numerous. |
| Shape | Spatulate lobed | Spatulate lobed. |
| Texture | Smooth | Smooth. |
| Ribs and veins | Very prominent | Prominent. |
| Edge | Deeply indented | Moderately indented. |
| Serration | Coarse | Fine. |
| Underside | Light green, 7.5GY5/4. | Light green, 7.5GY5/4. |
| Stipules | Rudimentary | Small. |

We claim.

1. A new and distinct cultivar of chrystanthemum characterized particularly as to its uniqueness when compared to the cultivar Carillon by its approximately one inch larger flower, with the flower having a higher crown and a more decorative flower form, a lighter flower color with less lavender tones, a more pointed petal tip, longer, broader, more deeply indented foliage with more prominent veins and a darker foliage color, more coarse serration to the leaf margin, smaller stipules, one week later response, and a more limited flowering period primarily designed for mid-winter performance.

No references cited.

UNITED STATES PATENT OFFICE

CERTIFICATE OF CORRECTION

Patent No. PP-3,248 Dated August 1, 1972

Inventor(s) WALTER H. JESSEL, JR. & WILLIAM E. DUFFETT

It is certified that error appears in the above-identified patent and that said Letters Patent are hereby corrected as shown below:

Column 2, before line 1, insert --BOTANICAL CLASSIFICATION: Chrysanthemum morifolium--;
Column 2, line 26, change "Peproductive" to --Reproductive--;
Column 2, line 30, change "Rant" to --Plant--.

Column 1, line 40, "progency" should read --progeny--.

Signed and sealed this 22nd day of May 1973.

(SEAL)
Attest:

EDWARD M.FLETCHER,JR.
Attesting Officer

ROBERT GOTTSCHALK
Commissioner of Patents

Dedication

PP. 3,248.—*Walter H. Jessel, Jr.*, Doylestown, and *William E. Duffett*, Akron, Ohio. CHRYSANTHEMUM PLANT. Patent dated Aug. 1, 1972. Dedication filed Feb. 6, 1975, by the assignee, *Yoder Brothers, Inc.* Hereby dedicates to the Public the entire remaining term of said patent.

[*Official Gazette July 1, 1975.*]